(12) United States Patent
Salters

(10) Patent No.: US 10,316,732 B2
(45) Date of Patent: Jun. 11, 2019

(54) ASSEMBLY COMPRISING A WET COMPARTMENT AND AT LEAST ONE ANTI-FOULING ENERGY SOURCE

(71) Applicant: KONINKLIJKE PHILIPS N.V., Eindhoven (NL)

(72) Inventor: Bart Andre Salters, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/579,748

(22) PCT Filed: May 31, 2016

(86) PCT No.: PCT/EP2016/062240
§ 371 (c)(1),
(2) Date: Dec. 5, 2017

(87) PCT Pub. No.: WO2016/198280
PCT Pub. Date: Dec. 15, 2016

(65) Prior Publication Data
US 2018/0179945 A1    Jun. 28, 2018

(30) Foreign Application Priority Data

Jun. 9, 2015 (EP) .................................... 15171197

(51) Int. Cl.
*F01P 11/06* (2006.01)
*A61L 2/10* (2006.01)
(Continued)

(52) U.S. Cl.
CPC ............... *F01P 11/06* (2013.01); *A61L 2/10* (2013.01); *B63B 59/04* (2013.01); *B63H 21/383* (2013.01);
(Continued)

(58) Field of Classification Search
CPC ... F01P 11/06; F01P 3/207; A61L 2/10; B64B 59/04; C02F 1/32; C02F 1/325;
(Continued)

(56) References Cited

U.S. PATENT DOCUMENTS 4,744,731 A    5/1988   Nakajima et al.
5,308,505 A *  5/1994   Titus ..................... A61L 2/0011
                                              210/745
(Continued)

FOREIGN PATENT DOCUMENTS

DE    102008029464 A1   1/2010
JP        63162089 A    7/1988
(Continued)

*Primary Examiner* — Eliza W Osenbaugh-Stewar

(57) ABSTRACT

An assembly comprises a wet compartment (100) having at least one inlet opening for allowing water to enter the wet compartment (100), a functional unit (2) located in the wet compartment (100), a dry area (200) which cannot be reached by water and which is outside of the wet compartment (100), a barrier (110) situated between the dry area (200) and the wet compartment (100), and at least one energy source (20) which is arranged and configured to emit energy for preventing biofouling of at least an exterior surface (17) of the functional unit (2), wherein the energy source (20) is arranged in the dry area (200), a path (112) being present between the dry area (200) and the wet compartment (100) for allowing energy emitted by the energy source (20) during operation thereof to reach the wet compartment (100), through the barrier (110).

15 Claims, 2 Drawing Sheets

(51) Int. Cl.
*C02F 1/32* (2006.01)
*F01P 3/20* (2006.01)
*F28F 19/00* (2006.01)
*F28D 1/02* (2006.01)
*B63B 59/04* (2006.01)
*B63H 21/38* (2006.01)
*C02F 103/00* (2006.01)
*C02F 103/02* (2006.01)
*C02F 103/08* (2006.01)

(52) U.S. Cl.
CPC ............. *C02F 1/325* (2013.01); *F01P 3/207* (2013.01); *F28D 1/022* (2013.01); *F28D 1/0206* (2013.01); *F28F 19/00* (2013.01); *B63B 2770/00* (2013.01); *C02F 2103/008* (2013.01); *C02F 2103/023* (2013.01); *C02F 2103/08* (2013.01); *C02F 2201/3221* (2013.01); *C02F 2201/3222* (2013.01); *C02F 2201/3224* (2013.01); *C02F 2201/3226* (2013.01); *C02F 2201/3227* (2013.01); *C02F 2201/3228* (2013.01); *C02F 2303/20* (2013.01); *F01P 2011/063* (2013.01); *F28F 2265/20* (2013.01)

(58) Field of Classification Search
CPC .... C02F 2303/20; F28D 1/0206; F28D 1/022; B63B 2770/00
See application file for complete search history.

(56) References Cited

U.S. PATENT DOCUMENTS

| | | |
|---|---|---|
| 5,441,179 A | 8/1995 | Marsh |
| 6,447,721 B1 | 9/2002 | Horton, III et al. |
| 2002/0162969 A1 | 11/2002 | Reed |
| 2010/0200769 A1 | 8/2010 | Matsuda et al. |
| 2011/0143000 A1 | 6/2011 | Fiset |
| 2013/0048877 A1* | 2/2013 | Thoren ............... G02B 6/102 |
| | | 250/492.1 |
| 2014/0353519 A1* | 12/2014 | Wang ................. A01K 63/04 |
| | | 250/435 |

FOREIGN PATENT DOCUMENTS

| | | |
|---|---|---|
| JP | 63194794 A | 8/1988 |
| JP | 1136668 U | 9/1989 |
| JP | 5033888 B2 | 5/1993 |
| JP | 6114420 A | 4/1994 |
| JP | 7037389 B2 | 4/1995 |
| JP | 7037389 U | 7/1995 |
| JP | 2007007232 A | 1/2007 |
| JP | 2012162252 A | 8/2012 |
| JP | 05033888 B2 | 9/2012 |
| JP | 2014125034 A | 7/2014 |
| WO | 2000038814 A1 | 7/2000 |
| WO | 2007096057 A2 | 8/2007 |
| WO | 2007109895 A1 | 10/2007 |
| WO | 2008152646 A2 | 12/2008 |
| WO | 2009153251 A2 | 12/2009 |
| WO | 2015077051 A1 | 5/2015 |

* cited by examiner

ASSEMBLY COMPRISING A WET COMPARTMENT AND AT LEAST ONE ANTI-FOULING ENERGY SOURCE

CROSS-REFERENCE TO PRIOR APPLICATIONS

This application is the U.S. National Phase application under 35 U.S.C. § 371 of International Application No. PCT/EP2016/062240, filed on 31 May 2016, which claims the benefit of European Patent Application No. 15171197.5, filed on 9 Jun. 2015. These applications are hereby incorporated by reference herein.

FIELD OF THE INVENTION

The invention relates to an assembly comprising a wet compartment having at least one inlet opening for allowing water to enter the wet compartment, a functional unit located in the wet compartment, and at least one energy source which is adapted to emit energy for preventing bio fouling of at least one surface as present in the wet compartment, including an exterior surface of the functional unit.

The invention furthermore relates to a vessel comprising the assembly as mentioned.

BACKGROUND OF THE INVENTION

A practical application of an assembly as mentioned is in an engine-driven ship which is equipped with a box cooler for cooling the fluid of an engine cooling system of the ship, the box cooler comprising a plurality of tubes for containing and transporting the fluid to be cooled in their interior. Typically, such a ship has a compartment for accommodating the tubes of the box cooler, wherein the compartment is defined by a portion of the hull of the ship and partition plates, and wherein entry and exit openings are arranged in the hull at the position of the compartment so that water can enter the compartment, flow over the tubes in the compartment, and exit the compartment through natural flow and/or under the influence of motion of the ship.

A box cooler is a specific type of heat exchanger which is designed for use in an engine-driven ship. For example, in the case of a tugboat having an installed engine power of 15 MW, one or more box coolers are applied for transferring heat in the order of 5 MW to the seawater. Usually, a box cooler comprises bundles of U-shaped tubes for conducting a fluid to be cooled, wherein ends of leg portions of the tubes are secured to a common plate having openings for providing access to both leg portions of each of the tubes. It is a very practical option to enable the box cooler to perform its cooling function by continuously exposing the tubes thereof to fresh seawater. However, the environment of a box cooler is ideally suited for a phenomenon known as biological fouling or biofouling, as the seawater is heated to a medium temperature in the vicinity of the tubes as a result of the heat exchange with the relatively hot fluid in the interior of the tubes, and the constant flow of water continuously brings in new nutrients and organisms which are known to cause biofouling.

In general, biofouling is the accumulation of microorganisms, plants, algae, small animals and the like on surfaces. According to some estimates, over 1,800 species comprising over 4,000 organisms are responsible for biofouling. Hence, biofouling is caused by a wide variety of organisms, and involves much more than an attachment of barnacles and seaweeds to surfaces. Biofouling is divided into micro fouling which includes biofilm formation and bacterial adhesion, and macro fouling which includes the attachment of larger organisms. Due to the distinct chemistry and biology that determine what prevents them from settling, organisms are also classified as being hard or soft. Hard fouling organisms include calcareous organisms such as barnacles, encrusting bryozoans, mollusks, polychaetes and other tube worms, and zebra mussels. Soft fouling organisms include non-calcareous organisms such as seaweed, hydroids, algae and biofilm "slime". Together, these organisms form a fouling community.

In several situations, bio fouling creates substantial problems. Bio fouling can cause machinery to stop working, water inlets to get clogged, and heat exchangers to suffer from reduced performance. Hence, the topic of anti-fouling, i.e. the process of removing or preventing bio fouling, is well-known. In industrial processes involving wetted surfaces, bio dispersants can be used to control biofouling. In less controlled environments, fouling organisms are killed or repelled with coatings using biocides, thermal treatments or pulses of energy. Nontoxic mechanical strategies that prevent organisms from attaching to a surface include choosing a material or coating for causing the surface to be slippery, or creating nanoscale surface topologies similar to the skin of sharks and dolphins which only offer poor anchor points.

Biofouling of box coolers causes severe problems. The main issue is a reduced heat transferring capability as layers of bio fouling are effective heat insulators. When the bio fouling layers are so thick that seawater can no longer circulate between adjacent tubes of the box cooler, an additional deteriorating effect on the heat transfer is obtained. Thus, biofouling of box coolers increases the risk of engine over-heating, so that ships need to slow down or ship engines get damaged.

Anti-fouling arrangements for cooling units that cool the water from a cooling water system of an engine-driven ship by means of seawater are known in the art. For example, DE 102008029464 relates to a box cooler for use in ships and on offshore platforms, comprising an integrated anti-fouling system for killing fouling organisms by means of an overheating process that can be regularly repeated. In particular, the box cooler is protected against microorganism fouling by continuously overheating a defined number of heat exchanger tubes without interrupting the cooling process, wherein waste heat from the cooling water may be used for doing so.

In general, it is known in the art to use ultraviolet light for removing/preventing the formation of biofilm on wet surfaces. For example, WO 2014/014779 discloses a system for reducing fouling of a surface of an optically transparent element subjected to a marine environment, including a LED for emitting ultraviolet radiation, a mount for directing emitted ultraviolet radiation toward the optically transparent element, and control circuitry for driving the LED.

When it comes to keeping the tubes of a box cooler free from bio fouling, it is possible to have a box cooler which is equipped with a plurality of ultraviolet light sources which are positioned in an effective arrangement with respect to the tubes so as to be capable of casting ultraviolet light over the entire exterior surface of the tubes with an intensity which is sufficient for obtaining the desired effect of keeping the tubes clean. Such a type of box cooler is very well suitable to be used in practice. Nevertheless, a number of problems are associated with the use of the ultraviolet light sources at positions in the box cooler and right outside the box cooler. In the first place, it is a fact that the ultraviolet light sources, or the casings of the ultraviolet sources if a type of energy source comprising an ultraviolet light source and a casing for accommodating the light source is applied, are contacted by water, namely the water which is used for cooling the tubes of the box cooler. It may even be so that the energy sources are submerged in water most of their lifetime. On the basis of this fact, it is necessary to use waterproof electrical cables and to provide for watertight connections. Furthermore, on the basis of this fact, the energy sources are susceptible to fouling themselves, especially fouling caused by mineral deposits. In the second place, the energy sources are very hard to replace, if it is at all possible to do so. The compartment of the ship where the box cooler is present can only be reached by divers from underneath the ship, or during dry docking of the ship. Replacing the energy sources under water is a bothersome job and includes challenges in the field of electrical connections.

SUMMARY OF THE INVENTION

It is an object of the invention to provide measures for alleviating the problems associated with the box cooler which is equipped with the plurality of energy sources as mentioned in the foregoing. In general, it is an object of the invention to provide measures involving improvements in respect of an assembly comprising a wet compartment having at least one inlet opening for allowing water to enter the wet compartment, and at least one energy source which is adapted to emit energy for preventing bio fouling of at least one surface as present in the wet compartment.

According to the invention, an assembly is provided which comprises a wet compartment having at least one inlet opening for allowing water to enter the wet compartment, a functional unit located in the wet compartment, a dry area which cannot be reached by water and which is outside of the wet compartment, a barrier situated between the dry area and the wet compartment, and at least one energy source which is arranged and configured to emit energy for preventing bio fouling of at least one surface as present in the wet compartment, including an exterior surface of the functional unit, wherein the energy source is arranged in the dry area, a path being present between the dry area and the wet compartment for allowing energy emitted by the energy source during operation thereof to reach the wet compartment, through the barrier.

In the assembly according to the invention, the energy source is arranged outside of the wet compartment. On the basis of the arrangement of the energy source in a dry area of the assembly, which is separated from the wet compartment by means of a barrier, the problems associated with the exposure of the energy source to water are solved. Furthermore, it is very well possible to have much easier access to the energy source when the energy source is present in a dry area instead of a wet compartment. For the sake of completeness, it is noted that the definition of the dry area as being an area which cannot be reached by water should be understood such as to be based on the assumption of normal circumstances. In fact, the dry area is an area which is not supposed to be reached by water, which does not alter the fact that the dry area might get wet under abnormal circumstances such as a shipwreck in case the assembly is applied in a ship. Furthermore, it is noted that the definition of the dry area as being outside of the wet compartment should be understood such as to exclude any isolated dry area extending through the wet compartment, i.e. being inside the wet compartment, such as the interior of a casing which may be part of the energy source. In particular, in the assembly according to the invention, the dry area may be present just outside of the wet compartment, adjacent the wet compartment, at least partially surrounding the wet compartment if appropriate, or may be present at a distance from the wet compartment, to mention a few practical examples. In the context of the invention, the term "compartment" should preferably understood such as to mean something like a separate room, section, or chamber.

The advantageous new arrangement of the energy source does not need to have a decreasing effect on the efficiency of the treatment of the surface(s) in the wet compartment to be kept clean, as the invention also provides for a path being present between the dry area and the wet compartment for allowing energy emitted by the energy source during operation thereof to reach the wet compartment, through the barrier. In many practical cases, the material of the barrier is adapted to avoid exposure of the dry area to water as present in the wet compartment, and needs to have a certain strength, involving a function in blocking transfer of energy emitted by the energy source during operation thereof from the dry area to the wet compartment as a side effect. When the invention is applied, a path which allows the energy to travel from the dry area to the wet compartment is realized, so that the invention offers an advantageous possibility of minimizing the decreasing influence of this side effect on the transfer of energy from the dry area to the wet compartment.

In general, the path as mentioned can be realized when at least a portion of the barrier is adapted to allow energy emitted by the energy source during operation thereof to pass therethrough. Thus, in a practical embodiment, the barrier may comprise a portion which is adapted to allow the energy to pass therethrough to a much higher extent than the rest of the barrier, wherein the much higher extent is even an infinite extent if the rest of the barrier has a function in totally blocking a transfer of the energy. For the sake of completeness, it is noted that the invention also includes a barrier which is entirely permeable to the energy. However, in many practical cases, having a material which meets all requirements of watertightness, strength and permeability to the energy cannot be found or is very expensive, so that it is preferred to have a barrier which is permeable to the energy only at one or more positions such as to allow for effective conveyance of the energy to the surface in the wet compartment to be kept free from biofouling.

The general constitution of the barrier as explained in the foregoing can be realized by providing the barrier with a window which is permeable to energy emitted by the energy source during operation thereof. In the framework of this possibility of having a window in the barrier, the energy source and the window may be positioned such as to allow the energy to reach the surface in the wet compartment to be kept free from biofouling. In practice, the energy source may have a generally elongated shape. For example, the energy source may be a tubular lamp for emitting ultraviolet light during operation thereof. In that case, it is advantageous if the window has a similar generally elongated shape, wherein the energy source is arranged close to the window so as to have maximum exposure of the energy source to the wet compartment through the window.

It many practical cases, it is advantageous for the assembly to comprise a plurality of energy sources. In such cases, the barrier may be provided with a plurality of windows which are permeable to energy emitted by the energy sources during operation thereof, wherein it is possible yet not essential for each window to be associated with another one of the energy sources. All options as mentioned in the foregoing with respect to the possible presence of a window in the barrier are equally applicable if the barrier is provided with a plurality of windows. The invention also covers a situation in which the barrier is provided with a plurality of windows, and in which only a single energy source is used, and a situation in which the barrier is provided with only a single window, and in which more than one energy source is used.

In order to have maximum efficiency of the anti-fouling function of the energy source, it may be practical for the assembly to comprise a reflector arrangement for directing energy emitted by the energy source during operation thereof towards the wet compartment. For example, the barrier may comprise a window, wherein the energy source is arranged close to the window, and wherein a reflector is arranged at a position behind the energy source, so as to reflect energy emitted by the energy source in a direction away from the window towards the window.

As an alternative option to being provided with at least one window, the barrier may be provided with at least one hole, wherein the assembly may comprise at least one optical fiber extending through the hole in the barrier, constituting an optical path between the dry area and the wet compartment. This option is especially applicable in case the energy source is adapted to emit energy of an optical nature, such as ultraviolet light as mentioned earlier. As is known per se, a suitable type of optical fiber is glass fiber. Generally speaking, the barrier may be provided with at least one hole, wherein the assembly may comprise at least one element extending between the wet compartment and the dry area, through the hole in the barrier, the element being capable of conveying energy emitted by the energy source during operation thereof. In a case in which the functional unit as present in the wet compartment comprises a number of tubes of a cooling apparatus or the like, it is advantageous for the element to have a portion which is present inside the wet compartment as well and which is wrapped around and/or in between the tubes. For example, the portion of the element may be wrapped around the tubes in a spiraling fashion. The arrangement of the element as mentioned here can actually be realized in practice if the element is sufficiently flexible, which is the case when the element comprises a glass fiber, for example.

The case in which the energy source comprises a light source which is adapted to emit ultraviolet light is a very practical one, as ultraviolet light is suitable to be used for keeping surfaces clean from biofouling. In such case, it is practical for the barrier to be provided with an optical window which is permeable to ultraviolet light. Such optical window may comprise any suitable type of material, wherein it is possible for the optical window to comprise material which is also present in a casing of the light source, in the situation that the energy source comprises both a light source and a casing for accommodating the light source. For example, the optical window may comprise a glass plate, which may particularly be a quartz glass plate. Depending on the size of the optical window, it is even possible for the optical window to comprise a special material such as $CaF_2$.

The light source may be a tubular lamp for emitting ultraviolet light as mentioned earlier. Other embodiments of the light source are also feasible within the framework of the invention, including an embodiment in which the light source is an ultraviolet laser, in which case the area of the optical window does not need to be larger than roughly 1 $mm^2$, and an embodiment in which the light source is an ultraviolet LED or comprises a combination of a number of ultraviolet LEDs.

One feasible application of the assembly according to the invention is in a vessel, as mentioned earlier, in which case the vessel may be equipped with a cooling apparatus, especially a box cooler, wherein the at least one energy source of the assembly may be used for preventing biofouling of an exterior surface of the tubes of the cooling apparatus. As is known from the field of box coolers, at least a part of the cooling apparatus may have a layered structure in which the tubes are arranged in tube layers, each tube layer including at least one tube. In particular, the tube layers may include a number of U-shaped tubes having a curved bottom portion and two substantially straight leg portions, wherein the tubes of a tube layer have mutually different sizes, ranging from a smallest tube to a largest tube, the smallest tube having a smallest radius of the bottom portion, and the largest tube having a largest radius of the bottom portion, wherein top sides of the leg portions of the tubes are at a similar level in the cooling apparatus, and wherein the leg portions of the tubes extend substantially parallel to each other. In order for the anti-fouling measures of the invention to be as effective as possible, it is advantageous for the design of the box cooler to be adapted in such a way that less tube layers are obtained, and to have more tubes extending alongside each other, so that the extent to which one tube is in the way of the anti-fouling energy to another tube is minimized. In case the anti-fouling energy source has a generally elongated shape, it is preferred for the energy source to be oriented substantially perpendicular to the orientation of the tubes. In respect of the possible application of the assembly according to the invention in a vessel it is furthermore noted that in that case, the barrier may be part of an interior wall structure of the vessel, which wall structure serves for delimiting compartments of the vessel from each other.

For the sake of completeness, the following is noted in respect of anti-fouling by using ultraviolet light. The anti-fouling means for producing the ultraviolet light may comprise light sources which are chosen to specifically emit ultraviolet light of the c type, which is also known as UVC light, and even more specifically, light with a wavelength roughly between 250 nm and 300 nm. It has been found that most fouling organisms are killed, rendered inactive, or rendered unable to reproduce by exposing them to a certain dose of the ultraviolet light. A typical intensity which appears to be suitable for realizing anti-fouling is 10 mW per square meter, to be applied continuously or at a suitable frequency. A very efficient source for producing UVC light is a low pressure mercury discharge lamp, in which an average of 35% of input power is converted to UVC power. Another useful type of lamp is a medium pressure mercury discharge lamp. The lamp may be equipped with an envelope of special glass for filtering out ozone-forming radiation. Furthermore, a dimmer may be used with the lamp if so desired. Other types of useful UVC lamps are dielectric barrier discharge lamps, which are known for providing very powerful ultraviolet light at various wavelengths and at high electrical-to-optical power efficiencies, and LEDs. In respect of the LEDs, it is noted that they can generally be included in relatively small packages and consume less power than other types of light sources. LEDs can be manufactured to emit (ultraviolet) light of various desired wavelengths, and their operating parameters, most notably the output power, can be controlled to a high degree.

The light sources for emitting ultraviolet light can be provided in the form of a tubular lamp, more or less comparable to a well-known TL (tube luminescent/fluorescent) lamp. For various known germicidal tubular UVC lamps, the electrical and mechanical properties are comparable to those properties of tubular lamps for producing visible light. This allows the UVC lamps to be operated in the same way as the well-known lamps, wherein an electronic or magnetic ballast/starter circuit may be used, for example.

A general advantage of using ultraviolet light for realizing anti-fouling is that the microorganisms are prevented from adhering and rooting on the surface of the functional unit to be kept clean. Contrariwise, when known poison dispersing coatings are applied, the anti-fouling effect is achieved by killing the microorganisms after they have adhered and rooted on the surface. Prevention of bio fouling by means of light treatment is preferred over removal of biofouling by means of light treatment, as the latter requires more input power and involves a higher risk that the light treatment is not sufficiently effective. In view of the fact that the light sources for producing ultraviolet light may be arranged and configured such that only a relatively low level of input power is needed, the light sources may be operated to continuously produce anti-fouling light across a large surface without extreme power requirements, or the light sources may be operated at a duty cycle, wherein the light sources are on for a certain percentage of a time interval, and off for the rest of the time interval, wherein the time interval may be chosen to be in the order of magnitude of minutes, hours, or whatever is appropriate in a given situation. As not much additional power is required, the light sources can be easily applied in existing structures.

When the invention is applied, the at least one energy source which is used for preventing biofouling of a surface is arranged in a dry area, whereas the surface is present in a wet compartment. On the basis of this fact, a lot of practical problems relating to an arrangement of the energy source in the wet compartment are solved, including problems related to maintenance and repair of the energy source, lifetime of the energy source, reliability of the energy source and costs. No additional measures are needed for realizing electrical connections of the energy source in a safe and reliable fashion, or for changing the energy source. Furthermore, since the energy source is in the dry area, the energy source is not susceptible to fouling.

The above-described and other aspects of the invention will be apparent from and elucidated with reference to the following detailed description of two embodiments of a portion of a ship comprising, among other things, a wet compartment, a dry area, a box cooler comprising a plurality of tubes, and a light source for casting anti-fouling light on an exterior surface of the tubes of the box cooler.

BRIEF DESCRIPTION OF THE DRAWINGS

The invention will now be explained in greater detail with reference to the figures, in which equal or similar parts are indicated by the same reference signs, and in which.

DETAILED DESCRIPTION OF THE EMBODIMENTS

Figure 1:
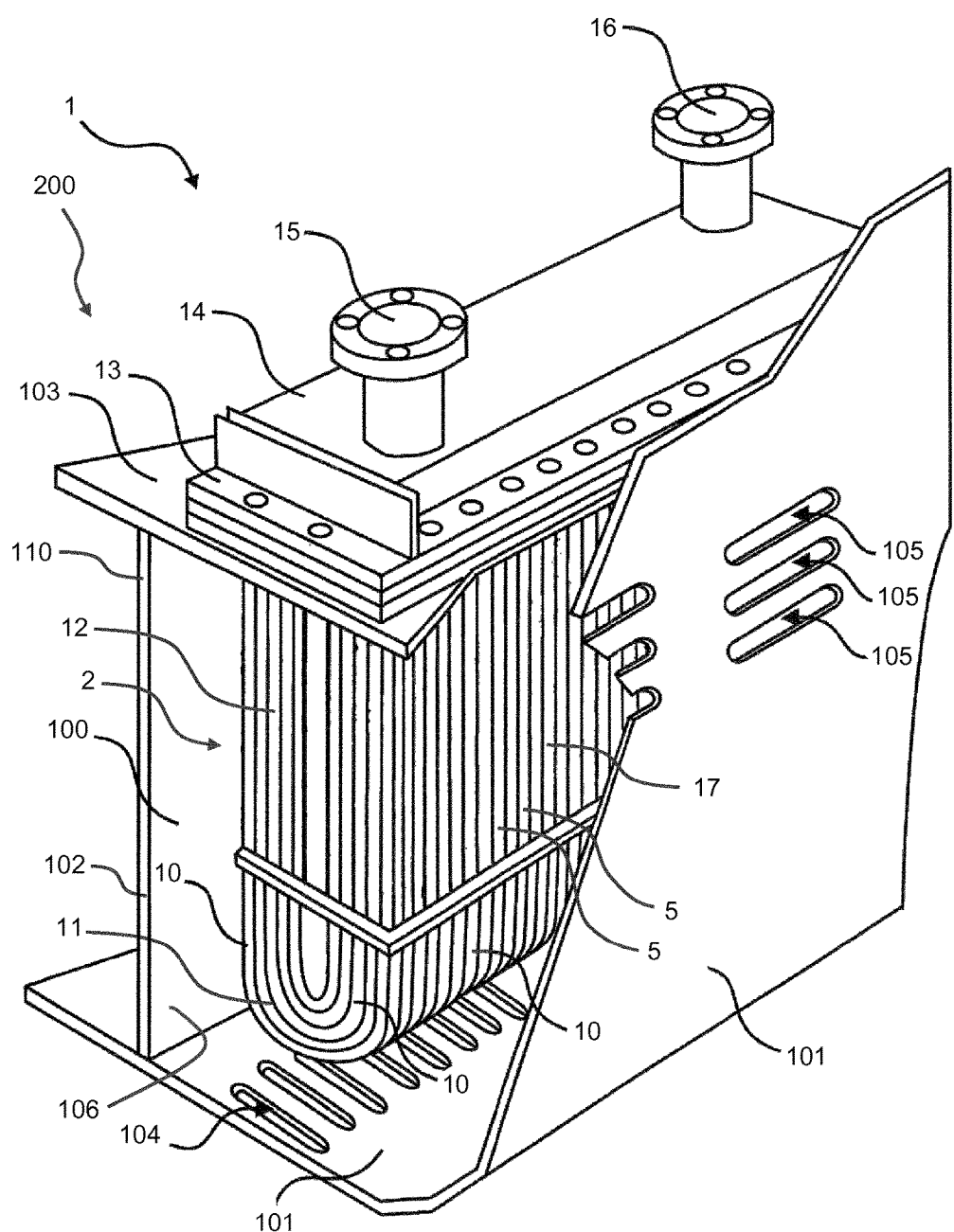
FIG. 1 diagrammatically shows a perspective view of a general example of a box cooler and a portion of walls delimiting a wet compartment of a ship in which an entirety of tubes of the box cooler is arranged.

FIG. 1 shows a general example of a box cooler 1 comprising a plurality of tubes 10 for containing and transporting a fluid to be cooled in their interior. The box cooler 1 is intended to be used in an engine-driven ship, wherein the fluid to be cooled is fluid from an engine cooling system of the ship, and wherein the box cooler 1 is enabled to perform its function of cooling the fluid by exposing the tubes 10 of the box cooler 1 to water from the immediate outside environment of the ship, which will hereinafter be referred to as seawater. In particular, the tubes 10 of the box cooler 1 are accommodated inside a wet compartment 100 of the ship, the wet compartment 100 being delimited by a portion of the ship's hull 101 and a number of partition plates 102, 103. In the shown example, the partition plates 102, 103 constitute a wall arrangement or barrier 110 between the wet compartment 100 and a dry area 200 of the ship, i.e. an area 200 of the ship which cannot be reached by the seawater, as the seawater is blocked by means of the partition plates 102, 103.

In the ship's hull 101, a number of entry openings 104 are arranged for allowing seawater to enter the wet compartment 100 from the outside, and a number of exit openings 105 are arranged in the ship's hull 101 as well, for allowing seawater to exit the wet compartment 100 and to flow to the outside of the ship. Typically, the entry openings 104 and the exit openings 105 are arranged at different levels, wherein the level of the entry openings 104 is lower than the level of the exit openings 105, assuming a normal, upright orientation of the ship, the wet compartment 100 and the box cooler 1 in conformity with FIG. 1. For the sake of completeness, it is noted that indications of directions, both explicit and implicit, as used in the following description are to be understood such as to have the normal, upright orientation of the ship, the wet compartment 100 and the box cooler 1 as mentioned as underlying assumption.

The tubes 10 of the box cooler 1 have a curved shape, particularly a U shape, comprising a curved bottom portion 11 and two substantially straight leg portions 12 extending substantially parallel to each other, in an upward direction with respect to the bottom portion 11. During operation of the box cooler 1, fluid to be cooled, i.e. hot fluid, flows through the tubes 10, while seawater enters the wet compartment 100 through the entry openings 104. On the basis of the interaction of the seawater with the tubes 10 containing the hot fluid, it happens that the tubes 10 and the fluid are cooled, and that the seawater heats up. On the basis of the latter effect, a natural flow of rising seawater is obtained in the wet compartment 100, wherein cold seawater enters the wet compartment 100 through the entry openings 104, and wherein seawater at a higher temperature exits the wet compartment 100 through the exit openings 105. Also, motion of the ship may contribute to the flow of seawater through the wet compartment 100. Advantageously, the tubes 10 are made of a material having good heat transferring capabilities, such as copper.

The tubes 10 of the box cooler 1 are arranged in similar, substantially parallel tube layers 5, each of those tube layers 5 comprising a number of tubes 10 of different size arranged in a bundle, wherein a smaller tube 10 is arranged inside of the curved shape of a larger tube 10, so as to be encompassed by a larger tube 10 at a certain distance for leaving space between the tubes 10 in the tube layer 5 where seawater can flow. Hence, each tube layer comprises a number of hairpin-type tubes 10 comprising two straight leg portions 12 and one curved portion 11. The tubes 10 are disposed with their curved portions 11 in substantially concentric arrangement and their leg portions 12 in substantially parallel arrangement, so that the innermost curved portions 11 are of relatively small radius of curvature and the outermost curved portions 11 are of relatively large radius of curvature, with at least one remaining intermediate curved portion 11 disposed therebetween. In case there are at least two intermediate curved portions 11, those portions 11 are of progressively graduated radius of curvature.

Top sides of the leg portions 12 of the tubes 10 are at a similar level in view of the fact that the top sides of the leg portions 12 of the tubes 10 are connected to a common tube plate 13. The tube plate 13 is covered by a fluid header 14 comprising at least one inlet stub 15 and at least one outlet stub 16 for the entry and the exit of fluid to and from the tubes 10, respectively. Hence, the leg portions 12 of the tubes 10 which are at the side of the inlet stub 15 are at the highest temperature, while the leg portions 12 of the tubes 10 which are at the side of the outlet stub 16 are at a lower temperature, and the same is applicable to the fluid flowing through the tubes 10.

During the continuous cooling process of the tubes 10 and the fluid as present in the tubes 10, any microorganisms being present in the seawater tend to attach to the tubes 10, especially the portions of the tubes 10 which are at an ideal temperature for providing a suitable environment for the microorganisms to live in, the phenomenon being known as biofouling. In order to prevent this phenomenon, it is proposed to use at least one light source 20 for casting anti-fouling light on an exterior surface 17 of the tubes 10. For example, the light may be UVC light, which is known to be effective for realizing anti-fouling.

Figure 2:
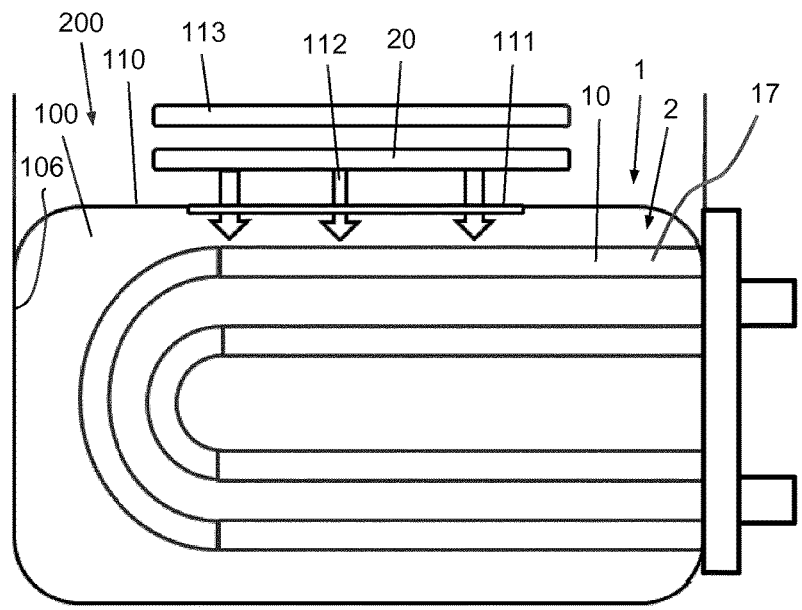
FIG. 2 diagrammatically shows the wet compartment of the ship, a dry area outside of the wet compartment, the box cooler, and a light source for casting anti-fouling light over the exterior surface of the tubes of the box cooler, in a first possible arrangement according to the invention.
Figure 3:
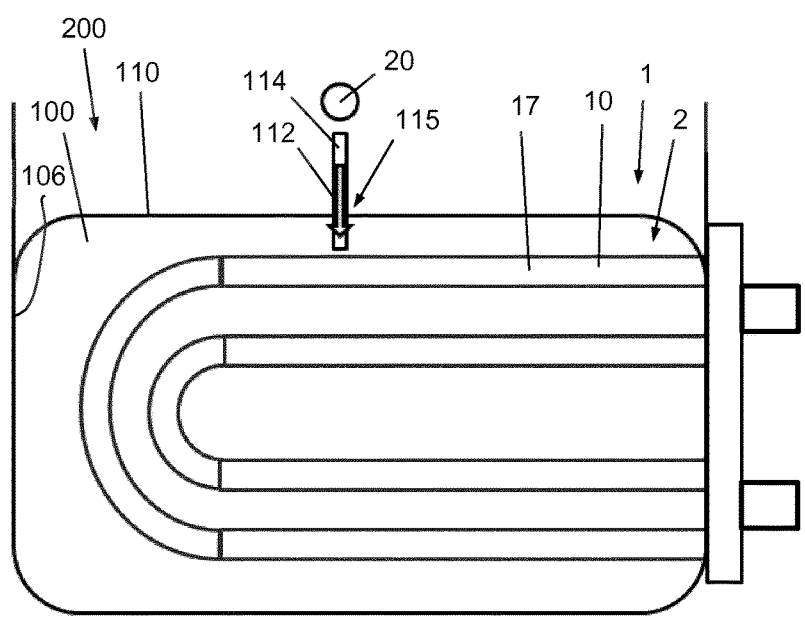
FIG. 3 diagrammatically shows the wet compartment of the ship, the dry area, the box cooler, and the light source, in a second possible arrangement according to the invention.

FIG. 2 and FIG. 3 illustrate the fact that the light source 20 is arranged in the dry area 200, outside of the wet compartment 100.

The light source 20 may be a tubular lamp having a generally elongated shape. FIG. 2 illustrates an arrangement in which such a type of light source 20 is used. In this arrangement, the light source 20 is situated close to the barrier 110, and a window 111 is present in the barrier 110 for allowing the ultraviolet light to pass through the barrier 110 at the position of the window 111. Hence, the window 111 is an optical window which is permeable to ultraviolet light. A path of the ultraviolet light from the dry area 200 to the wet compartment 100 is diagrammatically indicated in FIG. 2 by means of a series of arrows 112. Advantageously, the shape of the window 111 is adapted to the shape of the light source 20. Hence, in the shown example, the window 111 has a generally elongated shape, in a similar manner as the light source 20. In a practical situation, dimensions of the window 111 may be something like 20×100 cm, or 30×150 cm, for example. The window 111 may comprise a glass plate, possibly made of quartz material.

Optionally, at a position which is a position behind the light source 20 as seen from the wet compartment 100, a reflector arrangement 113 is present for ensuring optimum efficiency of the irradiation process of the exterior surface 17 of the tubes 10 of the box cooler 1. In general, various advantageous layouts are possible for ensuring that a substantial/maximum part of the ultraviolet light is directed onto the tubes 10. Also, one or more windows 111 can be used, in combination with one or more light sources 20.

FIG. 3 illustrates another possible arrangement existing within the framework of the invention. In this arrangement, the light source 20 is an ultraviolet laser. An optical fiber 114, particularly a glass fiber, is used for providing an optical path between the dry area 200 and the wet compartment 100, and extends between a position close to the light source 20 in the dry area 200 to a position close to the tubes 10 of the box cooler 1 in the wet compartment 100. The path of the ultraviolet light from the dry area 200 to the wet compartment 100 is diagrammatically indicated in FIG. 3 by means of an arrow 112. For the sake of completeness, it is noted that in this arrangement, the barrier 110 is provided with a hole 115 for allowing the optical fiber 114 to pass through the barrier 110 at the position of the hole 115. Furthermore, it is noted that in order to avoid leakage of water from the wet compartment 100 to the dry area 200 through the hole 115 in the barrier 110, suitable measures may be taken for having a watertight seal at the position of the periphery of the optical fiber 114.

The arrangements as shown in FIGS. 2 and 3 are just two of the many examples existing within the framework of the invention. The exterior surface 17 of tubes 10 of a box cooler 1 is just one example of an exterior surface of a functional unit 2 as may be present in a wet compartment 100, which is to be kept free from bio fouling. An interior surface 106 of the portion of the ship's hull 101 associated with the wet compartment 100 and/or the partition plates 102, 103 is an example of an additional surface which is to be kept clean from bio fouling. Furthermore, ultraviolet light is just one example of a type of energy which is suitable to be used for anti-fouling purposes. Hence, the invention is not restricted to the use of one or more light sources 20, but covers the use of any possible anti-fouling energy source. Although it is preferred to have an arrangement in which all of the energy sources used for anti-fouling purposes are situated in the dry area 200, the invention also covers an arrangement in which such energy sources are present in both the wet compartment 100 and the dry area 200.

The invention is applicable to a ship as described in the foregoing, to any other type of vessel comprising a wet compartment 100 and a dry area 200, or to any other assembly comprising a wet compartment 100 and a dry area 200, wherein a at least one functional unit 2 is present in the wet compartment 100, and wherein an exterior surface 17 of the unit(s) 2 needs to be kept clean from bio fouling. In a ship or other type of vessel, the dry area 200 is an area which is present in the vessel, and which cannot be reached by water. The dry area 200 may be present directly adjacent to the wet compartment 100, but this is not necessary within the framework of the invention. When the dry area 200 is situated at a certain distance from the wet compartment 100, the distance can be bridged by means of an element such as an optical fiber as mentioned earlier. The ship or other type of vessel, or the assembly in a more general sense may comprise more than one wet compartment 100 in which the invention is applied, i.e. in which at least one energy source 20 for emitting energy for anti-fouling purposes is arranged in a dry area 200 and is still capable of acting on the exterior surface of a functional unit 2 in the wet compartment 100, through a path 112 extending from the dry area 200 to the wet compartment 100.

It will be clear to a person skilled in the art that the scope of the invention is not limited to the examples discussed in the foregoing, but that several amendments and modifications thereof are possible without deviating from the scope of the invention as defined in the attached claims. It is intended that the invention be construed as including all such amendments and modifications insofar they come within the scope of the claims or the equivalents thereof. While the invention has been illustrated and described in detail in the figures and the description, such illustration and description are to be considered illustrative or exemplary only, and not restrictive. The invention is not limited to the disclosed embodiments. The drawings are schematic, wherein details that are not required for understanding the invention may have been omitted, and not necessarily to scale.

Variations to the disclosed embodiments can be understood and effected by a person skilled in the art in practicing the claimed invention, from a study of the figures, the description and the attached claims. In the claims, the word "comprising" does not exclude other steps or elements, and the indefinite article "a" or "an" does not exclude a plurality. Any reference signs in the claims should not be construed as limiting the scope of the invention. The phrase "a plurality of" as used in this text should be understood such as to mean "at least two".

Elements and aspects discussed for or in relation with a particular embodiment may be suitably combined with elements and aspects of other embodiments, unless explicitly stated otherwise. Thus, the mere fact that certain measures are recited in mutually different dependent claims does not indicate that a combination of these measures cannot be used to advantage.

The term "substantially" as used in this text will be understood by a person skilled in the art as being applicable to situations in which a certain effect is intended which can be fully realized in theory but which involves practical margins for its factual implementation. Examples of such an effect include a parallel arrangement of objects and a perpendicular arrangement of objects. Where applicable, the term "substantially" may be understood such as to be an adjective which is indicative of a percentage of 90% or higher, such as 95% or higher, especially 99% or higher, even more especially 99.5% or higher, including 100%.

The term "comprise" as used in this text will be understood by a person skilled in the art as covering the term "consist of". Hence, the term "comprise" may in respect of an embodiment mean "consist of", but may in another embodiment mean "contain/include at least the defined species and optionally one or more other species".

In view of the fact that bio fouling does not only occur at sea, but also in rivers, lakes and the like, the invention is generally applicable in a context in which a wet compartment 100 is present, which may be filled with any kind of water. This context may be the context of a vessel, as mentioned earlier, or even more general, the context of marine objects such as oilrigs, or other types of buildings in or next to the ocean.

In respect of the possible application of the invention in the context of a wet compartment 100 accommodating a box cooler 1, it is noted that the invention is in no way restricted to the layout of the box cooler 1 as described in the foregoing and illustrated in the figures as an example. It is clear to a person skilled in the art that the features of the invention are not dependent on any feature of the surface 17, 106 to be protected against the fouling effect of water. Also, the application of ultraviolet light sources 20 for realizing anti-fouling effects during operation thereof is just one of the many possibilities existing within the framework of the invention. In the embodiments of the invention as shown, the wet compartment 100 is used for accommodating an entirety 2 of the tubes 10 of a box cooler 1, which entirety 2 is just one example of a functional unit. Additionally or alternatively, the wet compartment 100 of the assembly according to the invention may be used for accommodating one or more other functional units, wherein it is noted that a functional unit should be understood such as to be a unit which is configured to perform one or more technical functions in the wet compartment 100 other than for instance merely constructional functions (functions directly related to the very presence of a unit as part of a construction, such as passive supporting functions or passive delimiting functions). In case the assembly is applied in a ship, the wet compartment 100 may be a so-called sea chest.

In the shown embodiment of the assembly according to the invention, the wet compartment 100 is provided with at least one entry opening 104 for allowing water to enter the wet compartment 100 and at least one exit opening 105 for allowing water to exit the wet compartment 100. That does not alter the fact that the option of only a single opening being present, wherein the opening has a combined function of being an entry opening and an exit opening, is also covered by the invention. For the sake of completeness, it is noted that it is not essential to have at least one exit opening 105, on the basis of the fact that practical cases exist in which there is no need for emptying the wet compartment 100 through one or more exit openings 105 after initial filling of the wet compartment 100.

Summarizing, an assembly comprises a wet compartment 100 having at least one inlet opening 104 for allowing water to enter the wet compartment 100, a functional unit 2 located in the wet compartment 100, a dry area 200 which cannot be reached by water and which is outside of the wet compartment 100, a barrier 110 situated between the dry area 200 and the wet compartment 100, and at least one energy source 20 which is arranged and configured to emit energy for preventing bio fouling of at least an exterior surface 17 of the functional unit 2, including an exterior surface of the functional unit, wherein the energy source 20 is arranged in the dry area 200, a path 112 being present between the dry area 200 and the wet compartment 100 for allowing energy emitted by the energy source 20 during operation thereof to reach the wet compartment 100, through the barrier 110. On the basis of these features of the assembly, it is achieved that any disadvantage associated with having the energy source 20 in a wet environment is avoided, while the possible blocking effect of the barrier 110 on the transport of energy from the energy source 20 to the wet compartment 100 is removed.

The invention claimed is:
1. An assembly comprising
   a wet compartment having at least one inlet opening for allowing water to enter the wet compartment,
   a functional unit located in the wet compartment, including an exterior surface,
   a dry area which cannot be reached by water and which is outside of the wet compartment,
   a barrier situated between the dry area and the wet compartment, and
   at least one energy source which is arranged and configured to emit energy for preventing biofouling of at least one surface as present in the wet compartment, including the exterior surface of the functional unit,
   wherein the energy source is arranged in the dry area, a path being present between the dry area and the wet compartment for allowing energy emitted by the energy source during operation thereof to reach the wet compartment, through the barrier, the functional unit being any hardware having an exterior surface in the wet compartment that the energy source is arranged to prevent biofouling of.

2. The assembly according to claim 1, wherein at least a portion of the barrier is adapted to allow energy emitted by the energy source during operation thereof to pass therethrough.

3. The assembly according to claim 1, wherein the barrier is provided with a window which is permeable to energy emitted by the energy source during operation thereof.

4. The assembly according to claim 3, wherein the energy source and the window are positioned so as to allow energy emitted by the energy source during operation thereof to reach the surface in the wet compartment to be kept free from biofouling.

5. The assembly according to claim 3, wherein the energy source has a generally elongated shape, wherein the window has a similar generally elongated shape, and wherein the energy source is arranged close to the window so as to have maximum exposure of the energy source to the wet compartment through the window.

6. The assembly according to claim 1, comprising a plurality of energy sources, wherein the barrier is provided with a plurality of windows which are permeable to energy emitted by the energy sources during operation thereof.

7. The assembly according to claim 1, comprising a reflector arrangement for directing energy emitted by the energy source during operation thereof towards the wet compartment.

8. The assembly according to claim 1, wherein the barrier is provided with at least one hole, and wherein the assembly comprises at least one element extending between the wet compartment and the dry area, through the hole in the barrier, the element being capable of conveying energy emitted by the energy source during operation thereof, and wherein optionally the element comprises an optical fiber for constituting an optical path between the dry area and the wet compartment.

9. The assembly according to claim 8, wherein the functional unit comprises a plurality of tubes, a portion of the element being wrapped around and/or in between the tubes.

10. The assembly according to claim 1, wherein the energy source comprises a light source which is adapted to emit ultraviolet light, the barrier being provided with an optical window which is permeable to ultraviolet light.

11. The assembly according to claim 10, wherein the energy source furthermore comprises a casing for accommodating the light source, and wherein optionally the window comprises material which is also present in the casing of the light source.

12. The assembly according to claim 1, wherein the surface in the wet compartment to be kept free from biofouling further includes an interior surface of walls delimiting the wet compartment.

13. A vessel comprising the assembly according to claim 1, wherein the barrier comprises a wall arrangement delimiting the wet compartment in combination with a portion of the vessel's hull.

14. The vessel according to claim 13, furthermore comprising an engine for driving the vessel, and an engine cooling system including a cooling apparatus, wherein the cooling apparatus comprises a plurality of tubes for containing and transporting fluid to be cooled in their interior, the tubes being intended to be at least partially exposed to water during operation of the cooling apparatus, wherein the functional unit located in the wet compartment comprises an entirety of the tubes of the cooling apparatus.

15. The vessel according to claim 14, wherein the surface in the wet compartment to be kept free from biofouling further includes an interior surface of walls delimiting the wet compartment.

* * * * *